United States Patent [19]
Araki et al.

[11] 4,219,258
[45] Aug. 26, 1980

[54] ILLUMINATING DEVICE FOR USE IN A FUNDUSCOPIC APPARATUS

[75] Inventors: Naomiki Araki; Yasuo Inoue, both of Hachioji, Japan

[73] Assignee: Olympus Optical Co., Ltd., Tokyo, Japan

[21] Appl. No.: 927,601

[22] Filed: Jul. 24, 1978

Related U.S. Application Data

[63] Continuation of Ser. No. 748,190, Dec. 7, 1976, abandoned.

[30] Foreign Application Priority Data

Feb. 10, 1975 [JP] Japan ................................ 50-116595

[51] Int. Cl.$^2$ .......................... A61B 3/10; A61B 3/14; G03B 29/00
[52] U.S. Cl. .......................................... 351/16; 351/7; 354/62
[58] Field of Search ....................... 351/16, 7; 354/62; 350/96

[56] References Cited

U.S. PATENT DOCUMENTS

| | | | |
|---|---|---|---|
| 3,556,085 | 1/1971 | Takahasi | 350/96 BC UX |
| 3,780,979 | 12/1973 | De Guillebon | 351/16 |
| 3,915,564 | 10/1975 | Urban | 351/7 |
| 4,023,189 | 5/1977 | Govignon | 351/7 |

*Primary Examiner*—John K. Corbin
*Assistant Examiner*—Rodney B. Bovernick
*Attorney, Agent, or Firm*—Kenyon & Kenyon

[57] ABSTRACT

An illuminating device for use in an ophthalmoscopic photographing apparatus comprising an objective lens system arranged near an eye to be inspected in a main optical viewing path, a photographing lens system arranged in the main optical path for imaging a light pattern reflected from the retina of the eye to be inspected on the surface of a film through the objective lens system, and a light guide arranged the main optical viewing path and an illuminating optical path. The light guide consists of a bundle of optical fibers one end portion of which is so constructed that a plurality of optical fibers uniformly enclose a light passing tube to form a concentric circle or partially enclose the light tube.

1 Claim, 5 Drawing Figures

ILLUMINATING DEVICE FOR USE IN A FUNDUSCOPIC APPARATUS

This is a continuation, of application Ser. No. 748,190 filed Dec. 7, 1976 now abandoned.

BACKGROUND OF THE INVENTION

1. Field of the Invention

The present invention relates to an illuminating device for use in a photographic apparatus of a fundus oculi.

2. Description of the Prior Art

An ophthalmoscopic photographic apparatus is used to inspect retinal hemorrhage, ablatio retinae, arteriosclerosis or the like. In the conventional photographic apparatus of fundus oculi the optical system thereof is as shown in FIG. 1, in which reference numeral 1 is a light source for observation, 2 is a condenser lens for observation, 3 is a light source for photographing, 4 is a condenser lens for photographing, 5 is a half-mirror, 6 is a ring slit, 7, 8 and 9 are lenses for illuminating, 10 is a reflecting mirror, 11 is a reflecting mirror with an aperture, 12 is an objective lens, 13 is an eye to be inspected, 14 is a photographic lens, 15 is a reflecting mirror for switching optical path, 16 is a reflecting prism, 17 is an ocular, and 18 is a film surface. In such a conventionally used photographic apparatus of fundus oculi, when observation is carried out with the use of a light source for observation, illumination light from the light source 1 for observation is reflected by the half-mirror 5 through the condenser lens 2 for observation so as to change its light path, and projected on the ring slit 6. Further, the illumination light passed through the ring slit 6 and the lens 7 is again changed its light path by the reflecting mirror 10, and then projected on the reflecting mirror 11 with the aperture by means of each lens 8, 9. Furthermore, the illuminating light reflected by the reflecting mirror 11 with the aperture is projected on the cornea of the eye 13 to be inspected by means of the objective lens 12 and then the light illuminates the retina of the eye to be inspected. Then, the light reflected by the retina passes again through the objective lens 12 and the light transmitted through the aperture of the reflecting mirror 11 is observed as an image of the retina by means of the ocular 17 through the lens 14, the reflecting mirror 15 and the reflecting prism 16.

On the other hand, in case of photographing, the illumination light for photographing emitted from the light source 3 passes through the half-mirror 5 by means of the condenser lens 4, and projected on the ring slit 6, so that the light illuminates the retina of the eye 13 to be inspected as explained in the case of the aforementioned observation. Further, the light reflected on the retina is also directed to the direction of the lens 14. In this case, the reflecting mirror 15 is switched to the position shown by a dotted line, so that the light reflected on the retina is focussed and imaged on the film surface 18 by means of the lens 14 and photographed.

In the conventional photographic apparatus of the fundus oculi explained in the above, both the illumination light from the light source 1 for observation and the illumination light from the light source 3 for photographing are projected on the ring slit 6 by means of the condenser lens 2 or the condenser lens 4, respectively, and then the light transmitted through the portion 6a of the ring slit 6 shown in FIG. 2 is utilized for illumination, but the light through other portion, for example the central portion 6b, is interrupted. However, strength of the light from the light source projected by the condenser lens is brightest at the center and darker around the periphery. Therefore, in the illuminating method for the conventional photographic apparatus of the fundus oculi, the brightest portion of the illumination light from the light source is cut off, so that such method is not efficient in the point of light strength. Further, this method uses the lenses 7, 8, 9 and the reflecting mirror 10 as an illumination optical system, so that a loss of a light amount due to reflection on the lens surface is present and not preferable.

Further, the ring slit 6 and the reflecting mirror 11 with the aperture are same in size, so that an image produced by the illumination optical systems 7, 8 and 9 of the ring slit 6 must be projected precisely on the reflecting surface of the reflecting mirror 11. Accordingly, there is such a problem that the ring slit 6, the reflecting mirror 11 with the aperture, the reflecting mirror 10, and the illuminating optical systems 7, 8, 9 must precisely be centered with each other.

SUMMARY OF THE INVENTION

An object of the present invention is to eliminate the above described defects of the conventional photographic apparatus of the fundus oculi.

Another object of the present invention is to provide an illuminating device for use in a photographic apparatus of a fundus oculi in which a light guide is used instead of a ring slit or the like.

An illuminating device according to the present invention comprise an objective lens system arranged near an eye to be inspected in a main optical viewing path, a photographing lens system arranged in the main optical path for focussing a light reflected from the retina of the eye to be inspected on the surface of a film through the objective lens system, and a light guide arranged between the main optical viewing path and an illuminating optical path. One end portion of the light guide is arranged between the objective lens system and the photographing lens system in the main optical path. The other end portion of the light guide is arranged near at least one light source in the illuminating optical path. The light guide consists of a bundle of optical fibers. At the one end portion of the light guide a plurality of optical fibers uniformly enclose a light passing tube so as to form a concentric circle. Alternatively, a plurality of optical fibers partially enclose the light passing tube.

DESCRIPTION OF THE PREFERRED EMBODIMENT

Figure 1:
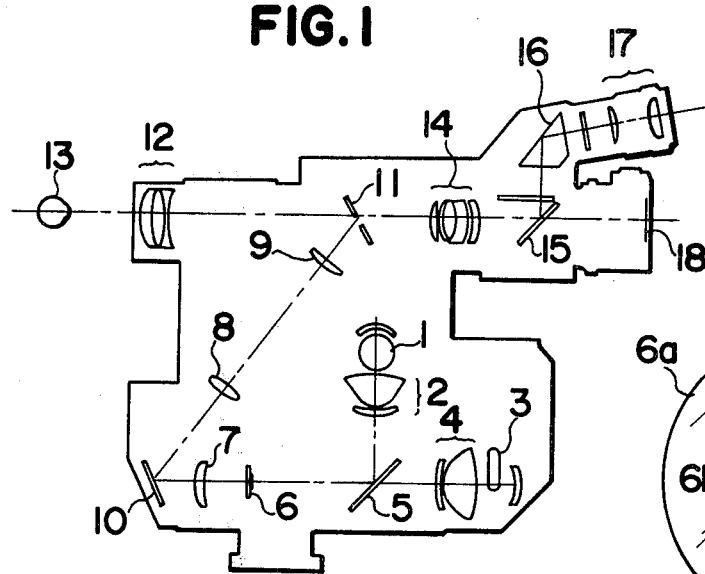
FIG. 1 shows an optical system of a conventional ophthalmoscopic photographic apparatus.
Figure 2:
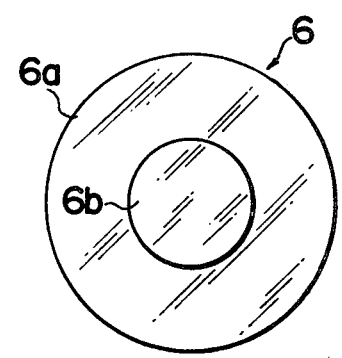
FIG. 2 shows a ring slit used for the conventional illuminating device.
Figure 3:
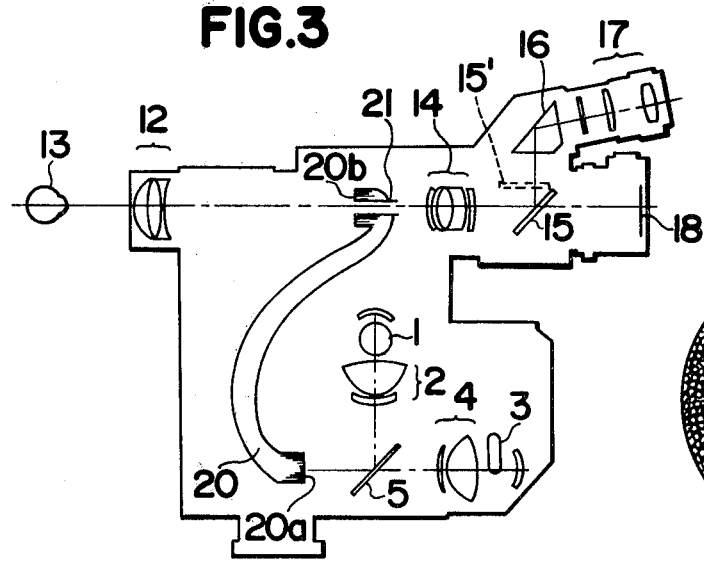
FIG. 3 shows an optical system of an ophthalmoscopic photographic apparatus provided with an illuminating device according to the present invention.

Referring now to FIG. 3 one embodiment of an illuminating device for use in a photographic apparatus of a fundus oculi is shown. Similar reference characters refer to similar elements or members in FIG. 1. In the present invention a light guide 20 is arranged between the position where the conventional ring slit is provided and the position where the conventional reflecting mirror with the aperture is provided. The arrangement of the other optical elements is substantially the same as that of the optical elements shown in FIG. 1 so that the detailed explanation thereof is emitted. The optical guide 20 consists of a bundle of optical fibers. The charactertics of the optical fiber are well known and the detailed explanation thereof is omitted.

Figure 5:
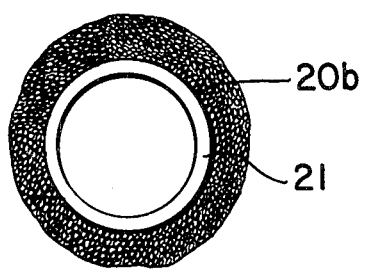
FIG. 5 shows an embodiment of another end portion of a light guide.

One end surface 20a of the light guide 20 is arranged at the projecting position of the condenser lens 2 or 4 of the light source 1 for observation or the light source 3 for photographing so as to include the projection image of the light source inclusive of the center thereof. Further, the other end 20b of the light guide 20 is arranged to uniformly enclose a tube 21 for transmitting the light reflected on the retina as illustrated by FIG. 5.

In the device according to the present invention as shown in FIG. 3 the illuminating light from the light source 1 for observation is projected on one end surface 20a of the light guide 20 by means of the condenser lens 2 for observation in case of observing with the naked eye. The illuminating light thus entered into one end surface 20a of the light guide 20 is transmitted to the other end 20b thereof and projected on the cornea of the eye 13 to be inspected by means of the objective lens 12 and then the light illuminates the retina of the eye to be inspected. Further, the light reflected by the retina is transmitted through the objective lens 12 and observed by the ocular 17 through the tube 21 in the same manner as in the conventional embodiment. Further, in case of photographing, the illuminating light from the light source 3 for photographing is projected on the end surface 20 of the light guide 20 by means of the condenser lens 4 for photographing, transmitted to the other end 20b, illuminated the retina of the eye 13 to be inspected and photographed in the same manner.

The present invention has the construction as explained in the foregoing, so that the illuminating light from the light source for observation or photographing can illuminate over the whole area of the end surface 20a of the light guide 20, and particularly, the central light part having larger strength can be utilized, and as a result, the illuminating light can effectively be utilized. Further, the light emitted from the other end 20b of the light guide arranged around the tube 21 never enters into the lens 14, so that there is no cause of flare. The illuminating device according to the present invention does not require any illuminating lens system nor reflecting mirror as required in the conventional device, so that there is no light loss due to these optical elements, and more effective bright illumination becomes possible. Further, since these optical elements are not used, only three elements, i.e., the objective lens 12, the photographic lens 14 and the tube 21 are exactly arranged on the same optical axis, and the end surface 20a of the light guide 20 is placed at the position of the ring slit, so that the device can easily be assembled. The light guide 20 is merely arranged at the proper position in the device other than both end portions thereof, so that the whole device can be made compact.

Figure 4:
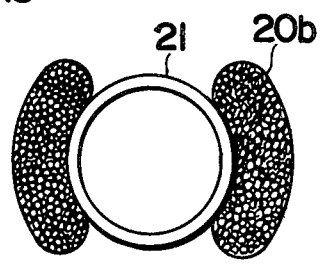
FIG. 4 shows an embodiment of one end portion of a light guide used in the illuminating device according to the present invention.

Further, one end surface 20b of the light guide 20 can be arranged in different shapes instead of a ring shape around the tube 21. For example, it is possible to arrange it around the tube 21 with a shape shown in FIG. 4. Further, if the light guide 20 is rotatably arranged around the tube 21, i.e., when the two portions of the end 20b shown on FIG. 4 are not secured to the tube 21, but can rotate thereon, the rotation of the light emitted from the end surface 20b can rotate a projecting image focussed on the cornea by the objective lens 12, so that a bad influence of a diffusion light caused by any around on the cornea can be removed.

Furthermore, the one end portion of the light guide 20 is divided into two, and the thus divided end portions are used by arranging near the light source for observation and the light source for photographing, respectively, without using the half-mirror 5.

What is claimed is:

1. In a photographic apparatus of a fundus oculi comprising an objective lens system arranged near an eye to be inspected in a main optical viewing path; a photographic lens system arranged in said main optical path for focusing light reflected from the retina of the eye to be inspected on the surface of a film through an objective lens system; at least one light source; and means for establishing an illuminating optical path between said light source and the main optical path such as to present an annulus of light surrounding said main optical path for illuminating the eye, the improvement comprising:
   (a) a light tube concentric about the main optical path disposed between the objective lens system and the photographic lens system; and
   (b) a light guide consisting of a bundle of optical fibers having one end portion arranged so as to partially enclose said light tube forming a partial annulus thereabout, said one end of said bundle of fibers being disposed for rotation about said tube and the other end of said bundle of optical fibers arranged near said at least one light source in the illuminating optical path, whereby alignment of the elements in the optical light path is less critical and the light from said at least one light source can be used more efficiently, and whereby through the use of said bundle of said optical fibers only partically encircling said tube and being mounted for rotation thereon the projection image on the cornea of the eye to be examined by the objective lens system can be rotated to remove a bad influence on diffusion of light.

* * * * *